United States Patent [19]

Watanabe

[11] Patent Number: 4,902,489

[45] Date of Patent: Feb. 20, 1990

[54] METHOD FOR DEODORIZING AND CLEANING OFFENSIVE ODOR GAS

[75] Inventor: Toshihiro Watanabe, Tokyo, Japan

[73] Assignee: Sankyo Kogyo Co., Ltd., Tokyo, Japan

[21] Appl. No.: 273,088

[22] Filed: Nov. 18, 1988

[51] Int. Cl.⁴ .................... B01J 8/00; C10H 23/00; C01B 17/16; C01C 3/00

[52] U.S. Cl. ..................... 423/245.1; 423/245.2; 423/228; 423/238

[58] Field of Search ............. 423/245.1, 245.2, 238, 423/228

[56] References Cited

U.S. PATENT DOCUMENTS

| | | | |
|---|---|---|---|
| 769,860 | 9/1904 | Felt | 423/245.2 |
| 3,907,972 | 9/1975 | Staatzenberger | 423/243 |
| 3,989,810 | 11/1976 | Toyama et al. | 423/226 |
| 4,127,383 | 11/1978 | Johnston et al. | 422/5 |
| 4,136,152 | 1/1979 | Jones et al. | 423/242 |
| 4,427,630 | 1/1984 | Aibe et al. | 423/245.1 |
| 4,540,561 | 9/1985 | Olson | 423/226 |
| 4,551,305 | 11/1985 | Nelson | 422/5 |

OTHER PUBLICATIONS

Patent Abstract of Japan, vol. 4, No. 135 (C-25) [617], Sep. 20, 1980, (see 55-84539).

Patent Abstract of Japan, vol. 8, No. 232 (C-248 [1669], Oct. 25, 1984.

*Primary Examiner*—Gregory A. Heller

*Attorney, Agent, or Firm*—Birch, Stewart, Kolasch & Birch

[57] ABSTRACT

The present invention relates to for deodorizing and cleaning offensive gas which comprises treatment with a lignin solution after washing the gas to remove basic offensive ingredients. The method is excellent in efficiency of deodorization and maintenance cost especially for offensive odor ingredients that are hard to decompose.

11 Claims, 2 Drawing Sheets

METHOD FOR DEODORIZING AND CLEANING OFFENSIVE ODOR GAS

BACKGROUND OF THE INVENTION (1) Field of the Invention

The present invention relates to a system for continuously deodorizing and cleaning gas that contains offensive odor ingredients.

(2) Description of the Prior Art

Conventionally, adsorption methods using activated carbon or cleaning methods using a strong oxidizing agent have been typically used for removing sulfur compounds, which are known to be difficult to decompose.

Unfortunately, deodorizers such as activated carbon that have been conventionally used have very low adsorption capacities, with the result that they are ineffective against various offensive odor ingredients. Also, the use of an oxidizing agent requires great skill to accurately match the amount of oxidizing agent used to the concentration of the offensive ingredient.

Gas generated in a sewage treatment plant, a night soil treatment plant, or the like, widely varies in concentration and emits a composite odor. Accordingly, such conventional deodorizers as described above are not suitable to deodorize such malodorous gas. Thus another approach to deodorization has been desired.

In view of the above, various methods for treating foul-smelling gas were proposed. For treating the composite gas discharged from a night soil treatment plant, for example, an oxidizing method using a mixture of a sodium hypochlorite solution and a sodium hydroxide solution, an adsorption method using activated carbon, or the combination of these two methods has been used widely. However, the adsorption treatment with activated carbon results in the maintenance cost being so high that it is often impractical. A sodium hypochlorite solution generally deteriorates over time, rendering its long-term storage difficult. Also, use of the solution requires great skill to accurately control the proper solution to match the concentration of the malodorous ingredient of the gas. Further, the gas emitted from a sodium hypochlorite solution itself contains an offensive and irritating ingredient, which often causes secondary environmental pollution.

In addition, a considerable amount of foul odor remains in the gas treated by the above mentioned proposed method, which means a high fume stack is required to widely diffuse the gas discharged therefrom.

Accordingly, it has been highly desired to develop a method for efficiently deodorizing and cleaning offensive odor ingredients that are hard to decompose by a low-cost method that does not use activated carbon or an oxidizing agent.

In particular, in order to treat malodorous gas at a high removal rate without causing secondary offensive ingredients emitted from a sodium hypochlorite solution to remain in the treated gas, it is necessary to accurately control the amount of treatment chemical corresponding to the wide variation of the initial concentration of the malodorous ingredient. However, such control is not only impractical, it is frequently necessary to replace the treatment chemical.

In order to stabilize the concentration of gas after treatment and to prolong the serviceable time of the adsorbent such as activated carbon or the like, it would be possible to increase the amount of the adsorbent to be filled. However, it fails to decrease the cost of the adsorbent, because the adsorption is carried out in a physical manner. Also, it increases the pressure loss in proportion to the amount of filled adsorbent leading to an increase in operation cost, resulting in failing to improve the maintenance.

Moreover, composite malodorous gas varies greatly in its concentration and composition depending on the time of the year, so that the conventional treatment methods fail to accommodate such variations of composite gas.

BRIEF SUMMARY OF THE INVENTION

Accordingly, it is an object of the present invention to provide a method for deodorizing and cleaning offensive odor ingredients that are difficult to decompose from a gas with high efficiency and at low cost.

It is another object of the present invention to provide a method for efficiently deodorizing and cleaning malodorous gas that widely varies in its concentration of offensive composite odor.

It is a further object of the present invention to provide a method for deodorizing and cleaning malodorous gas using a compact, unitized type of system.

The above and other objects, features, and advantages of the invention will become apparent in the following description and drawings.

DETAILED DESCRIPTION OF THE INVENTION

Figure 1:
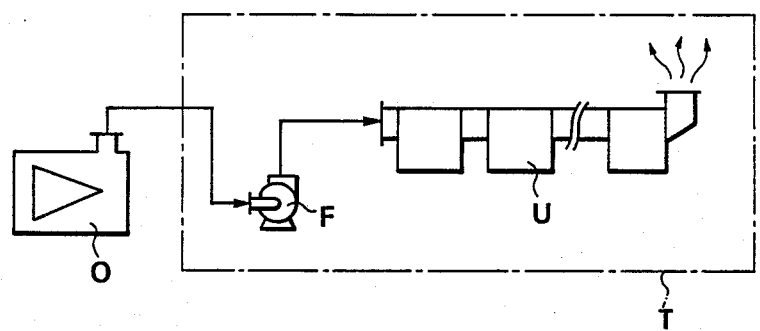
FIG. 1 is a diagrammatic view showing an example of a plant adapted to use the method of the present invention for night soil treatment.

The present invention has been made taking notice of the fact that composite malodorous gas is cleaned with very high efficiency and continuously with an organic acid solution and a lignin-sulfonate solution in turn, and it is the result of much effort by the inventors to eliminate the foregoing disadvantages of the prior art.

More specifically, the present invention provides a method for deodorizing and cleaning malodorous gas, which comprises the steps of washing the gas to remove the basic offensive ingredients and then treating it with an activated lignin solution.

The treatment method of the present invention is not limited to any specific gas. For example, the present invention is applicable to malodorous gas emitted from night soil, in addition to offensive gas from sewage, stock farms, feed plants, fertilizer plants, waste disposal plants, and the like. Foul-smelling gas discharged from a surplus sludge treatment system of a night soil treatment plant has a composition of, for example, 65 ppm or less hydrogen sulfide, 27 ppm ammonia, 0.0001 ppm or less trimethylamine, 6.2 ppm methyl mercaptan, 1.7 ppm methyl sulfide, and 0.19 ppm methyl disulfide.

In the present invention, basic ingredients contained in malodorous gas are first removed. The removal may be carried out by a suitable means such as, for example, washing with water or acid. In particular, treatment with an organic acid solution is effective for removing basic offensive ingredients in terms of the removal speed, reliability, consumption and nontoxicity of the treatment agent, and the like.

Organic acids which may be used for this purpose include citric acid, acetic acid, caproic acid, mesotartaric acid, mesaconic acid, and the like. Citric acid and acetic acid are particularly preferable for this purpose. It is most preferable to combine citric acid with a small amount of acetic acid. The organic acid solution is preferably in the form of an aqueous solution. In general, the concentration of the solution is preferably 0.01 mol or more, more preferably 0.03 mol or more, although it varies depending on the concentration or content of the basic ingredients in the offensive gas.

The treatment of the gas with an organic acid solution or the like causes the basic ingredients contained in the malodorous gas, such as, for example, ammonia, amines, or the like, to be effectively removed from the gas.

Subsequent to removal of the basic offensive ingredients, the gas is subjected to a treatment with an aqueous lignin solution. The aqueous lignin solution may be prepared using lignin solubilized through sulfonation, or the like.

In the present invention, the aqueous lignin solution may be obtained by suitably dissolving water-solubilized lignin in water. The concentration of lignin in the solution is preferably 0.05% by weight or more and is more preferably 0.2% by weight or more. The concentration does not have an upper limit, however, it is preferably about 1.5 percent by weight or less, in view of cost. The solution has a pH of preferably 9 to 11, more preferably 9.5 to 10.0.

Lignin, which is preferably used for this purpose in the present invention, takes the form of a liquid of lignin-sulfonate obtained by purifying pulp waste liquid discharged from a paper mill and suitably adjusting the pH of the liquid or its salt.

An example of the composition is shown in Table 1.

TABLE 1

|  | Softwood (wt. %) | Hardwood (wt. %) |
|---|---|---|
| Lignin-sulfonate | 50–55 | 40–45 |
| Monosaccharide:Hexose | 16–20 | 3–5 |
| Monosaccharide:Pentose | 3–5 | 15–20 |
| Modified Saccharide | 15–20 | 15–20 |
| Organic Acid Furfural | 2–4 | 10–15 |
| Inorganic Matter | 5–10 | 5–10 |

The treatment of foul-smelling gas with a so-prepared lignin solution causes foul-smelling acidic ingredients in the gas, such as, for example, hydrogen sulfide, methyl mercaptan, methyl sulfide, or the like to be substantially removed therefrom.

Treatment with a lignin solution after removal of the basic ingredients is essential in the system of the present invention. However, a treatment such as washing of the gas with acid after treatment with a lignin solution causes the rate of removal of the lignin solution to be substantially reduced.

In the present invention, the use of an alkaline salt in the lignin solution causes the activity of the solution to be further stabilized. The alkaline salt used for this purpose preferably takes the form of carbonate. Also, the salt used is in an amount preferably twice or more, more preferably five to ten times as much, as the lignin, by weight.

Also in the present invention, a suitable increase in the number of treatment-steps (units) with the lignin solution permits the removal of substantially all malodorous ingredients from the gas.

Further, as a modified embodiment of the present invention, a washing treatment with a conventional agent is carried out between the washing treatment with the above-described acid and that with the lignin solution. Alternatively, any conventional treatment known in the art may take place subsequent to the treatment with the lignin solution.

Now the present invention will be described with reference to the drawings.

FIG. 1 is a diagrammatic view showing an example of a plant for practicing the method of the present invention, wherein reference character 0 designates the source of release of foul-smelling gas in the sludge treatment system of a night soil treatment plant, F is a gas suction blower, and T is a deodorization system for practicing the method of the present invention. In the deodorization system T, reference character U designates a deodorization unit used for the present invention. An example of deodorization unit U is shown in detail in FIG. 2, wherein P-1 and P-2 each indicate units for removing a basic ingredient from malodorous gas, T-1 to T-4 each indicate treatment units using a lignin solution, and S-1 and S-2 each are preparatory units.

The arrows indicate the direction of the flow of malodorous gas.

Preparatory units S-1 and S-2 are each used to store a treatment liquid suitably selected, depending on the volume of gas and the concentration of the offensive ingredients in the gas. The gas-liquid contact that takes place between the malodorous gas and the treating liquid in each of units P-1 and P-2, T-1 to T-4, and S-1 and S-2 is not limited to any specific manner, and a conventional gas-liquid contact system, a leak shelf system, or the like. However, a system that may be preferably used for this purpose in the present invention includes a gas-liquid contact apparatus disclosed in U.S. Pat. No. 4,775,499, filed by the applicant, which may be constructed, for example, in the manner as shown in FIG. 3.

Figure 3:
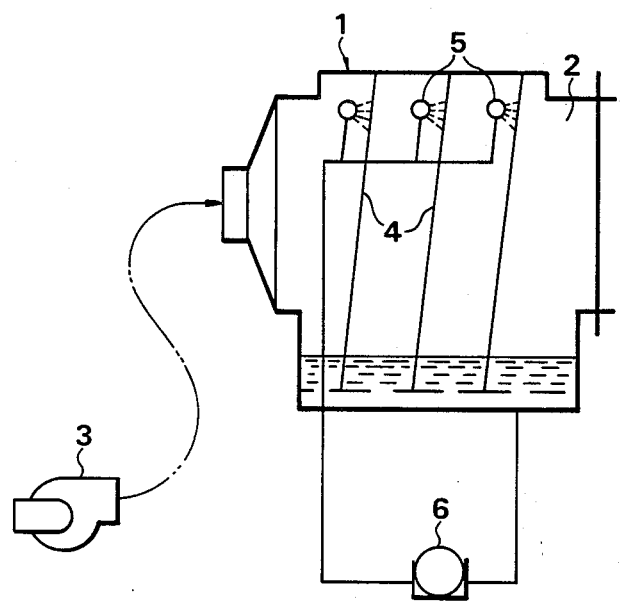
FIG. 3 is a schematic view showing an example of a gas-liquid contact apparatus.

More particularly, the gas-liquid contact apparatus generally designated by reference numeral 1 in FIG. 3 includes a gas passage 2, a blower 3 provided in association with gas passage 2, screens 4 arranged in gas passage 2, liquid pouring devices 5 arranged in gas passage 2 for pouring liquid on the screens 4, and a pump 6 for returning liquid following downward through the screens 4 to the liquid pouring devices 5. Screens 4 may each be a flat screen comprising rods and wires arranged on the rods in parallel with one another at suitable intervals. Each of the screens 4 is positioned so as to fortress the gas passage 2 and cause the wires to be maintained in a horizontal orientation. Each screen 4 may be arranged at an angle $\alpha$ of 70 to 85 degrees with respect to the horizontal direction. However, the angle is not limited to such a degree, so long a film of liquid is formed all over the screen when the liquid is continuously poured on the screen. The angle is varied depending on the shape of the wires, the interval between the wires, the flow velocity of the gas to be treated, and the like. Pump 6 is provided in association with the passage for communicating the gas passage 2 and the liquid pouring device 5 with each other.

The pouring of liquid on each of the screens 4 by device 5, as shown in FIG. 3, is carried out with respect to the uppermost portion of the screen, so that the liquid may successively flow down through the screen, resulting in it spreading all over the screen.

It has been observed in the present invention that as a result of the odor removing treatment of a sulfur compound using a lignin solution over a period of time, the sulfur separates in the treatment unit. Thus, it is considered that there is not only the adsorptive action of the lignin solution, but also a chemical reaction between the lignin solution and the sulfur compound causing decomposition of the sulfur compound, separating out the sulfur alone.

According to the present invention, it is possible to composite the malodorous gas generated in a night soil treatment plant or the like with very high efficiency.

In particular, the method of the present invention can remove mercaptan, which is difficult to solubilize and decompose, and which is an ingredient in acidic gas, at a highly improved rate of stable removal. Further, the method of the present invention can be practiced in a manner highly compacted to a degree sufficient to exhibit great utility, because the method has a very high buffer ability on the variation in the concentration of malodorous gas.

As described below in the examples, it was found that the treatment according to the method of the present invention permits it to be substantially below 300 odor concentration units, which was considered to be the lowermost limit achieved by a conventional washing treatment with a chemical, such that a conventional treatment with a sodium hypochlorite solution by an expert results in the concentration of odor in the treated gas being as high as about 500 odor concentration units.

The lignin solution for use in the present invention can be used in a very small amount and it exhibits high stability as compared with a sodium hypochlorite solution, resulting in the storage or supplemental tank for the solution being quite small. Also, according to the present invention, it is possible to effectively clean the offensive gas, leading to the elimination of a fume stack. Further, the present invention can be safely practiced, because the lignin solution itself is safe, nontoxic, and substantially odorless.

Moreover, the method of the present invention permits each stage in the treatment to be practiced in a unit system. This permits the number of units used to be automatically controlled or varied depending on the concentration of the odor contained in foul-smelling gas and the treatment time, which results in saving energy. Also, this permits the liquid in each unit to perform efficiently.

Next, the present invention will be described in further detail in accordance with examples. In the examples, an initial concentration of malodorous gas and a concentration of the gas from which a basic ingredient was removed were determined by a gas-detector with a detector-tube made by Gastec Co. (Japan). Also, analysis by gas chromatography was suitably carried out to correct an error in determination caused by the detector-tube.

The concentration of odor in the treated gas was below the measurement capacity of the detector-tube throughout the test. Accordingly, the concentration was measured using an olfactory analysis (Susumu Kunibe: *Atarashii Dassyuqijutsu*, pp. 235-242, Kabushiki Kaisha Kogyo Chosakai, Oct. 1, 1981), and is indicated in odor concentration units.

EXAMPLE 1

Figure 2:
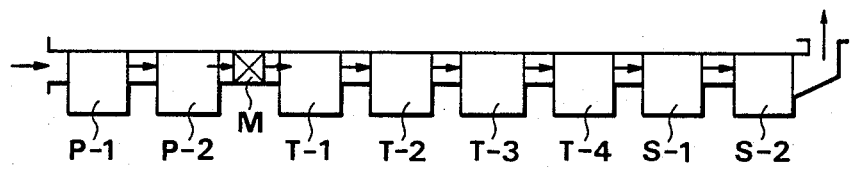
FIG. 2 is a block diagram showing an example of a deodorization system used for practicing the present invention.

Composite gas generated in a night soil treatment plant (hereinafter referred to as "original gas") was treated using the deodorization system shown in FIG. 2.

The treatment solution in each of the units in the deodorization system and the conditions for operating the unit were as follows:

Each of units P-1 and P-2 was charged with 50 l of 0.05M citric acid solution as the treatment solution. Replenishment or replacement of the treatment solution was not done during the test.

Units T-1 to T-4 were charged with 50 l of a treatment solution prepared by adding water to a lignin solution (lignin-sulfonate solution in which the concentration of lignin-sulfonate is 0.3% by weight) and then adding carbonate in an amount of 2.4% by weight to the solution. The treatment solution was not replenished or replaced during the test. Each of the units P-1 and P-2, and T-1 to T-4 consisted of the gas-liquid contact apparatus above-described with reference to FIG. 3, and the above-described citric acid or lignin solution was circulated in the gas-liquid contact apparatus. The conditions for driving the unit were as follows:

| (1) | Flow rate of treated gas | 2 $Nm^3$/min |
|---|---|---|
| (2) | Flow rate of circulated solution | 50 l/min · unit |
| (3) | Liquid-gas ratio | 25 l/$m^3$ · min |
| (4) | Volume of charged solution | 50 l |
| (5) | Gas-liquid contact screen | |
| | Dimension of screen | 170 mm width, 170 mm length |
| | Effective aperture area | 0.0289 $m^2$ |
| (6) | Gas velocity at gas-liquid contact | about 3 m/sec |

Units S-1 and S-2 were charged with clear water, which was not circulated.

The original gas was introduced into the P unit of the thus-constituted deodorization system and continuous operation took place for a long period of time to treat the gas.

The concentrations of gas at both the inlet and outlet of the P unit, measured 24 hours after starting the operation, are shown in Table 2.

TABLE 2

| | (ppm except*) | |
|---|---|---|
| | Inlet of P unit | Outlet of P unit |
| Ammonia | 24 | 0.2> |
| Trimethylamine | 0.0001> | 0.0001> |
| Hydrogen sulfide | 12 | 12 |
| Methyl mercaptan | 2.2 | 1.9 |
| Methyl sulfide | 4.7 | 4.4 |
| Methyl disulfide | 0.31 | 0.27 |
| Concentration of odor | 98,000* | 73,000* |

The concentrations of each of the ingredients in the treated gas at the inlet and the outlet of the T unit, measured five days after starting the operation, are shown in Table 3, which indicates that the rate of removal of each ingredient was extremely high.

TABLE 3

| | (ppm except*) | |
|---|---|---|
| | Inlet of T unit | Outlet of T unit |
| Ammonia | 0.2> | 0.2> |
| Trimethylamine | 0.0001> | 0.0001> |
| Hydrogen sulfide | 16 | 0.001> |
| Methyl mercaptan | 3.2 | 0.001> |
| Methyl sulfide | 4.4 | 0.002> |
| Methyl disulfide | 0.38 | 0.002> |

TABLE 3-continued

|  | (ppm except*) | |
| --- | --- | --- |
|  | Inlet of T unit | Outlet of T unit |
| Concentration of odor | 73,000* | 170* |

The pH of the lignin solution when the operation started was 10.4, whereas it was reduced to 9.65 after a lapse of four hours and to 9.5 after 18 hours. Thereafter it was maintained at 9.5. This reduction of the pH of the lignin solution did not affect the treated gas.

The results of this example indicates that the lignin solution was fully suitable for practical use.

REFERENCE EXAMPLE

Example 1 was substantially repeated, except that the original gas was directly introduced into the T unit without being passed through the P unit.

The concentrations of each ingredient in the gas at the inlet and outlet of the T unit, measured one (1) hour, 6 hours, and 24 hours after starting the operation, are respectively shown in Table 4, Table 5, and Table 6.

TABLE 4

|  | (ppm except*) | |
| --- | --- | --- |
|  | Inlet of T unit | Outlet of T unit |
| Ammonia | 30.5 | 0.22 |
| Trimethylamine | 0.0003 | 0.0001> |
| Hydrogen sulfide | 21 | 0.001> |
| Methyl mercaptan | 4.5 | 0.001> |
| Methyl sulfide | 6.0 | 0.001> |
| Methyl disulfide | 0.40 | 0.002> |
| Concentration of odor | 98,000* | 310* |
| pH of treating solution |  | 10.2* |

TABLE 5

|  | (ppm except*) | |
| --- | --- | --- |
|  | Inlet of T unit | Outlet of T unit |
| Ammonia | 24 | 0.28 |
| Trimethylamine | 0.0001 | 0.0001 |
| Hydrogen sulfide | 17.5 | 0.001> |
| Methyl mercaptan | 3.6 | 0.004 |
| Methyl sulfide | 4.9 | 0.007 |
| Methyl disulfide | 0.33 | 0.011 |
| Concentration of odor | 98,000* | 4,100* |
| pH of treating solution |  | 10.2* |

TABLE 6

|  | (ppm except*) | |
| --- | --- | --- |
|  | Inlet of T unit | Outlet of T unit |
| Ammonia | 20.5 | 10.5 |
| Trimethylamine | 0.0001 | 0.0001 |
| Hydrogen sulfide | 12 | 6.3 |
| Methyl mercaptan | 2.1 | 1.2 |
| Methyl sulfide | 4.3 | 2.4 |
| Methyl disulfide | 0.32 | 0.30 |
| Concentration of odor | 73,000* | 23,000* |
| pH of treating solution |  | 10.2* |

As can be seen from Tables 4, 5, and 6, the pH of the treatment solution was maintained at 10.2. However, the leakage of a sulfur compound was observed 6 hours after starting the operation, and it was impossible to carry out the treatment 24 hours after starting of the operation.

COMPARATIVE EXAMPLE

A test was carried out in connection with activated carbon, which was conventionally used as a deodorizer for removing odors of low concentration, and which is capable of reducing the concentration of an odor to a level below 300 odor concentration units. The equilibrium adsorption capacity of activated carbon with respect to malodorous ingredients is considered to be 8 to 10% by weight for hydrogen sulfide and 3 to 5% by weight for methyl mercaptan, and the example was operated while setting a break point at 20%. Therefore, the removable amount of hydrogen sulfide would be 1.6 to 2.0% by weight and that of methyl mercaptan would be 0.6 to 1.0% by weight. In view of this data, the time during which the treatment can be conducted with activated carbon in the same amount (150 grams) as lignin is contained in a lignin solution was calculated.

The calculation was carried out based on the concentration at the inlet of the T unit listed on Table 2, and the other conditions were as follows:

| (1) | Flow rate of treated gas | 2 Nm$^3$/min |
| --- | --- | --- |
| (2) | Temperature of gas | 25° C. |
| (3) | Molecular weight of H$_2$S | 34 |
|  | Molecular weight of CH$_3$SH | 48 |
| (4) | Absorption efficiency of activated carbon | 95% |

The break times of hydrogen sulfide (H$_2$S) and methyl mercaptan (CH$_3$SH) obtained under the calculation basis and conditions were as follows:

Hydrogen sulfide: 1.2 to 1.5 hours

Methyl mercaptan: 1.7 to 2.9 hours

As is apparent from the above calculation, it was found that activated carbon was disabled in about 2 hours. Thus, the lignin solution used in the present invention is highly superior to activated carbon.

Having described our invention as related to an embodiment, it is our intention that the invention not be limited by any of the details of the description, unless otherwise specified, but rather be construed broadly within its spirit and scope as set out in the accompanying claims.

What we claim is:

1. A method for deodorizing and cleaning offensive composite malodorous gas containing basic ingredients and sulfur compounds, which comprises the steps of washing the gas with an organic acid solution to remove basic offensive ingredients and then treating with a lignin-sulfonate solution.

2. The method as claimed in claim 1, wherein the organic acid is selected from the group consisting of citric acid, acetic acid, caproic acid, mesotartaric acid, and mesaconic acid.

3. The method as claimed in claim 1, wherein the concentration of lignin in the lignin-sulfonate solution is in the range of 0.05 to 1.5% by weight.

4. The method as claimed in claim 1, wherein the pH of lignin sulfonate solution is in the range of 9 to 11.

5. The method as claimed in claim 1, wherein the lignin sulfonate solution contains an alkaline salt.

6. The method as claimed in claim 1, wherein the offensive gas is a gas emitted from a night soil treatment.

7. The method as claimed in claim 1, wherein the concentration of the organic acid solution is at least 0.01 mol.

8. The method as claimed in claim 1, wherein the basic offensive ingredient is ammonia or amines.

9. The method as claimed in claim I, wherein the treatment with a lignin-sulfonate solution removes acidic ingredients in the offensive composite malodorous gas selected from the group consisting of hydrogen sulfide, methyl mercaptan and methyl sulfide.

10. The method as claimed in claim 5, wherein the alkaline salt is a carbonate thereof.

11. The method as claimed in claim 5, wherein the alkaline salt is present in at least twice the amount by weight of the lignin-sulfonate solution.

* * * * *